United States Patent
Tsao

(10) Patent No.: US 6,939,511 B2
(45) Date of Patent: *Sep. 6, 2005

(54) CONTACT LENS TREATING METHOD AND COMPOSITION

(75) Inventor: Fu-Pao Tsao, Lawrenceville, GA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/405,846

(22) Filed: Apr. 2, 2003

(65) Prior Publication Data

US 2004/0071591 A1 Apr. 15, 2004

Related U.S. Application Data

(62) Division of application No. 09/778,563, filed on Feb. 7, 2001, now Pat. No. 6,569,824.
(60) Provisional application No. 60/183,068, filed on Feb. 16, 2000.

(51) Int. Cl.$^7$ ............................................. C11D 40/00
(52) U.S. Cl. ........................ 422/28; 510/112; 510/113; 514/840
(58) Field of Search ........................... 422/28; 510/112, 510/113; 514/840

(56) References Cited

U.S. PATENT DOCUMENTS 6,569,824 B2 * 5/2003 Tsao ........................... 510/112

* cited by examiner

Primary Examiner—Krisanne Jastrzab
(74) Attorney, Agent, or Firm—Jian S. Zhou; Robert Gorman

(57) ABSTRACT

A method and composition for disinfecting a contact lens is disclosed. The method includes treating a lens with an aqueous solution having reduced toxicity to the eye which contains an effective amount of a monoperphthalic acid compound in a concentration of less than about 0.5% by weight of the solution. The lens disinfecting solution is capable of disinfecting contact lenses without irritating the eye due to reduced toxicity of the composition.

9 Claims, No Drawings

CONTACT LENS TREATING METHOD AND COMPOSITION

This application is a divisional of application Ser. No. 09/778,563, filed Feb. 7, 2001, issued as U.S. Pat. No. 6,569,824; which application claimed priority under 35 USC 119(e) to U.S. Provisional Application 60/183,068, filed Feb. 16, 2000.

FIELD OF THE INVENTION

This invention relates to a contact lens treating method and composition. In particular, the invention is directed to a contact lens disinfecting composition having reduced toxicity to the eye, wherein the composition comprises a monoperphthalic acid compound in a concentration of less than about 0.5% by weight of said composition.

BACKGROUND OF THE INVENTION

Contact lenses are worn on the cornea of the eye to improve sight. Both hard and soft contact lenses require periodic cleaning and disinfecting to remove protein deposits and undesirable microbes from the surface of the lens. In most cases, the lens is removed from the eye and cleaned with a lens cleaning solution. Then, the lens is disinfected. After disinfection, the lens usually is rinsed with saline solution for placement into the eye.

In the disinfecting of contact lenses, it is very important to select compositions that are effective to disinfect the lens but are not toxic to the eye. Thousands of compositions exist which are capable of disinfecting, but which exhibit toxic or undesirable discomfort to the eye when such compositions are used on lenses. Lens users sometimes fail to rinse the disinfectant solution from their lenses before placing lenses back into the eye. In some cases, lens wearers rinse their lenses poorly. Sometimes, the disinfecting composition adheres or adsorbs into the lens itself, such that even after a rinse, the relatively toxic substances from the disinfectant solution still may be temporarily retained within the surface of the lens. When that occurs, the toxic substances may be released into the eye once the lens is re-inserted. For these reasons, a desirable disinfectant solution preferably does not contain any compositions in concentration levels that exceed toxicity limits for the eye.

Unfortunately, many ophthalmic and lens care products which are effective disinfectants cause undesirable eye irritation. Also, many antimicrobial agents have a relatively narrow spectrum, and may be effective against certain microbes such as bacteria, but not against others such as fungi. Other compositions may be effective against a wide range of bacteria, yeast, and fungi, but may have limited efficacy. Many compositions that would otherwise be good lens disinfectant compositions undesirably react with other components in the lens care solution, producing unwanted side reactions and undesirable reaction products.

Magnesium perphthalate has been used in various medical applications, including contact lens disinfecting solutions. Magnesium perphthalate is a peroxy compound, and is known to have antimicrobial activity against bacteria and yeast.

Great Britain Patent 2,178,189A discloses the use of a monoperoxyphthalate salt such as magnesium monoperoxyphthalate hexahydrate in a contact lens cleaning solution. The patent teaches using magnesium monoperoxyphthalate hexahydrate in an amount from 1% to 20% by weight in aqueous solution. Another patent publication (WO 87/01562) discloses using alkaline earth metal salts of monoperphthalic acid for contact lens maintenance in aqueous concentration ranges between 0.5% and 10.0% by weight.

It recently has been discovered, however, that using such compounds in concentration ranges of 0.5% and above may have substantially adverse toxic effects to the user. Significantly elevated toxicity levels are experienced using lens care solutions having magnesium perphthalate concentrations of 0.5% or greater.

Recent data indicates that using such compounds in concentration levels below 0.5% provide surprisingly and unexpectedly reduced levels of toxicity, while still providing good lens disinfection.

ADDITIONAL BACKGROUND REFERENCES

European Patent Application 27,693, published Apr. 29, 1981, owned by Interox Chemicals Limited, discloses the magnesium salts of peroxycarboxylic acids, including the magnesium salt of monoperphthalic acid, and processes for preparing these compounds. The compounds are used as bleaching agents in washing compositions.

European Patent Application 96,525, published Dec. 21, 1983, owned by Interox Chemicals Limited, discloses compositions containing magnesium salts of organic peroxy acid/carboxylate compounds, including magnesium monoperphthalate. These compositions are used for the cleansing and sanitization of reusable diapers.

Great Britain Patent Application 2,137,882, published Oct. 17, 1984, owned by Interox Chemicals Limited, discloses disinfectants containing magnesium peroxycarboxylates, including magnesium monoperphthalate. Such compositions are used for disinfecting/sterilizing hard surfaces such as toilets, drains, or equipment used in medical or food processing environments.

U.S. Pat. No. 4,490,269, issued Dec. 25, 1984 to Gallopo discloses cleansing compositions comprising an effervescent agent and a monoperphthalate, or an effervescent agent and a potassium monopersulfate and a monoperphthalate, as bleaching agents. These compositions are used to cleanse removable orthodontic appliances such as false teeth, dental plates and bridges.

European Patent Application 133,354 published Feb. 20, 1985, owned by Interox Chemicals Limited discloses compositions, generally in tablet form, containing a peroxygen compound (including monoperphthalate) and an effervescence generator. These compositions are dissolved in water to produce a bath in which to soak, and thereby cleanse, removable dentures.

U.S. Pat. No. 3,988,433, issued Oct. 26, 1976 to Benedict, and Great Britain Patent 1,477,691, issued Oct. 19, 1977 to Jones et al., disclose compositions containing alkyl and aryl peroxy acids. These compositions are used to remove stains from teeth.

U.S. Pat. No. 4,350,681, issued Sep. 21, 1982 to Fulton, discloses compositions containing benzoyl peroxide stabilized in an aqueous medium by the presence of glycerol. These compositions are used as toothpastes or body scrubs.

SUMMARY OF THE INVENTION

Surprisingly, it has been discovered that using perphthalic acid compounds in concentration levels below 0.5% provides reduced levels of toxicity while still providing unexpectedly good lens disinfection.

The invention is directed to a contact lens treating method and composition. In particular, the invention is directed to a contact lens disinfecting composition having reduced toxicity to the eye, wherein the composition comprises a monoperphthalic acid compound in a concentration of less than about 0.5% by weight of said composition.

In the invention, methods and compositions are provided. In some cases, lens care disinfectant solutions are disclosed. Other embodiments provide a powder or tablet containing a monoperphthalic acid compound wherein the powder or tablet may be dissolved in an aqueous environment such as deionized water or saline solution just prior to soaking a contact lens in the solution. One convenient method of using the invention is to provide such powder or tablet with standard saline solution for disinfecting lenses, so that a lens wearer may use solutions already on hand and commercially available to perform the disinfecting operation.

One embodiment of the invention is a method of employing a composition wherein the monoperphthalic acid compound is selected from the group of compounds consisting of the following: magnesium monoperphthalate hexahydrate, magnesium monoperoxyphthalate hydrates, calcium monoperphthalate, sodium monoperphthalates, sodium monoperoxyphthalates, potassium monoperphthalates, potassium monoperoxyphthalates, magnesium perphthalates, calcium perphthalates, potassium perphthalates, sodium perphthalates, sodium potassium perphthalates, potassium hydrogen perphthalates, sodium hydrogen perphthalate, potassium acid perphthalates, perphthalic acid, monoperphthalic acid, magnesium perphthalate hexahydrates, perphthalate hydrates, 1,2 benzenedicarboperoxoic acid alkali metal salts, 1,2 benzenedicarboperoxoic acid dialkali metal salts, 2-carboxy benzenecarboperoxoic acid salts, 2-carboxy benzenemonocarboperoxoic acid alkaline earth metal salts, 2-carboxy benzenemonocarboperoxoic acid alkali metal salts, 2-carboxy benzenemonocarboperoxoic acid alkali metal hydrate salts, 2-carboxy benzenemonocarboperoxoic acid alkaline earth metal hydrate salts, 3-carboxy benzenemonocarboperoxoic acid alkali metal salts, 3-carboxy benzenemonocarboperoxoic acid alkali metal hydrate salts, 3-carboxy benzenemonocarboperoxoic acid alkaline metal hexahydrate salts, 3-carboxy benzenemonocarboperoxoic acid alkaline metal salts, 4-carboxy benzenemonocarboperoxoic acid alkali metal hexahydrate salts, 4-carboxy benzenemonocarboperoxoic acid alkali metal salts, 4-carboxy benzenemonocarboperoxoic acid alkaline metal hydrate salts, 4-carboxy benzenemonocarboperoxoic acid alkaline metal salts, 5-carboxy benzenemonocarboperoxoic acid alkali metal salts, 5-carboxy benzenemonocarboperoxoic acid alkali metal hydrate salts, 5-carboxy benzenemonocarboperoxoic acid alkaline metal salts, 5-carboxy benzenemonocarboperoxoic acid alkaline metal hydrate salts, 1,2-benzene dicarboperoxoic acid alkaline earth metal salts, 1,2-benzene dicarboperoxoic acid alkaline earth metal hydrate salts, 1,2-benzene dicarboperoxoic acid monoalkali metal salts, 1,2-benzene dicarboperoxoic acid dialkali metal salts, 1,2-benzene dicarboperoxoic acid, 1,3-benzene dicarboperoxoic acid alkaline earth metal salts, 1,3 benzene dicarboperoxoic acid, 1,3-benzene dicarboperoxoic acid monoalkali metal salts, 1,3-benzene dicarboperoxoic acid dialkali metal salts, 1,4-benzene dicarboperoxoic acid, 1,4-benzene dicarboperoxoic acid monoalkali metal salts, 1,4-benzene dicarboperoxoic acid dialkali metal salts, 1,4-benzene dicarboperoxoic acid alkeline earth metal salts, 1,5-benzene dicarboperoxoic acid, 1,5-benzene dicarboperoxoic acid monoaliali metal salts, 1,5-benzene dicarboperoxoic acid dialkali metal salts, and 1,5-benzene dicarboperoxoic acid alkaline earth metal salts.

One embodiment of the compositions of this invention utilizes magnesium perphthalate hexahydrate. There are numerous related compounds which are capable of providing the advantages of this invention, and the invention is not limited to only those compounds specifically provided herein. Practice of the invention and laboratory experience in cleaning and disinfecting lens solutions would reveal to a person of skill in the art other compositions and variants of the invention which may not be specifically listed, but would be within the scope and contemplation of this invention.

In another embodiment of the invention, an aqueous contact lens treating composition is provided comprising less than about 0.5% by weight of a compound having the general structure:

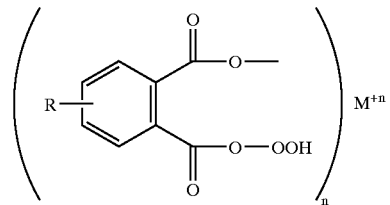

or its pharmaceutically acceptable salts or esters, wherein $M^{+n}$ is a cation selected from the group consisting of an alkali metal, an alkaline earth metal, a nontoxic heavy metal, trimethyl ammonium, a quaternary ammonium compound, and triethylammonium, and R is 1 or more substituents compatible with the peroxy acid functionality of the aromatic ring. The alkaline earth metal may be magnesium.

A contact lens is also disclosed, in which the lens has been treated with the compositions of this invention. Hard or soft lenses may benefit from disinfection with compositions of this invention. The invention contemplates dry granular compositions which in some instances may be added to aqueous solutions of saline or deionized water for lens disinfecting operations. Other embodiments of the invention include wet compositions that are packaged and sold as self contained, ready-made products for disinfecting lenses. The compositions employed to disinfect lenses have reduced toxicity.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

The following description provides an overview of the invention and test results indicating the efficacy and reduced toxicity of compositions of this invention. Examples of lens solutions and their methods of use are provided.

In the lens treating compositions of this invention, a weak acid and corresponding alkali metal or alkaline earth salt may be provided to the lens disinfection composition. In many cases, the acid used is boric acid, but other relatively weak acids such as phosphoric acids, citric acids, tartaric acids, carbonic acids, tromethamine hydrochloric acids, amino acids, acetic acids, other organic acids, other physiologically compatible weak acids and their corresponding alkali metal, alkaline earth metal salts or organic cationic ions (such as quaternary ammonium ions) can be substituted.

A primary goal is to make a buffer solution at an appropriate and physiologically acceptable pH range. Suitable buffering systems include the following acid systems: boric acid, phosphoric acids, citric acids, tartaric acids, carbonic acids, bi-carbonic acids, amino acids, tromethamine hydrochloric acids and the corresponding alkali metal or alkaline earth metal borates, citrates, phosphates, tartarates, acetates, carbonates, bicarbonates, amino acid salts, tromethamine salts and mixtures or combinations thereof. The concentration of the buffer may be easily modified and specified by those of skill in the art who are familiar with such buffering systems.

Further, the solution may contain a nonionic detergent such as a polyethylene oxide to improve wettability and cleaning effectiveness of the solution. The solution may also contain either saline or deionized water, and a buffer. The buffer may be made by dissolving a mixture of a weak acid and corresponding salts in isotonic buffered saline solution. Suitable water soluble salts compatible with ocular tissue include especially those salts conventionally employed in providing solutions having a salt content equivalent to about 0.9% sodium chloride (to make isotonic buffer saline solution). Preferred salts include alkali metal halides, sulfates, nitrates and phosphates, but this group is not limiting of the scope of this invention. Suitable water soluble polyols compatible with ocular tissue could be whole or partially replaced or substituted to adjust the isotonic solution.

In one embodiment of the invention, magnesium monoperoxyphthalate hexahydrate is employed. This compound is commercially available as Interox H48 from Interox Chemicals Limited of Warrington, Cheshire, England, or alternatively may be purchased in the United States from Aldrich Chemical of Milwaukee, Wis. 53201. This compound is freely soluble and is effective at room temperature. Other salts, such as for example, sodium or potassium salts may be employed.

The monoperoxyphthalate is preferably used in a concentration less than about 0.5% by weight in the aqueous solution, and may also be used in a concentration of about 0.25% or less by weight.

This compositions of this invention can be used to disinfect soft lenses, RGP lenses and hard lenses, i.e. lenses of glass or methyl methacrylate, or soft lenses such as those made of hydroxyethyl methacrylate (i.e. "HEMA") or from crosslinked copolymers of methyl methacrylate with hydrophilic comonomers, i.e. polyvinyl pyrrolidone.

In many cases, the aqueous solution may be mixed shortly before use by dissolving a tablet or powder in buffered saline solution. In a desirable formulation, a powder for dissolution contains approximately from about 5% to about 30% by weight magnesium monoperoxyphthalate hexahydrate and from about 70% to about 95% by weight detergent, protease, binders, fillers, lubricants, disintegrating agents, antiadherant, and glidants.

In the case of a tablet, it is possible to employ a single layer or multi-layered tablet having a controlled release coating built into the tablet to control the release sequence and pH of the final solution. Coating agents and pH adjustment agents as known to a person of skill in the art could be employed as well, including those listed herein. A coating agent such as "Eudragits", an acrylic copolymer distributed by Rohm America of Piscataway, N.J. could be employed. Other suitable coating agents that may be employed in the invention (and their respective suppliers) include: Shellac (Emcoat, Emerson Resources, Inc., Norristown, Pa.); Cellulose acetate phthalates (Eastman Chemical Co., Kingsport, Tenn. and FMC Corporation of Philadelphia, Pa.): HPMCP (Hydroxypropyl methylcellulose phthalate) (Eastman Chemical and Shin Etsu Chemical, Tokyo, Japan); Polyvinyl acetate phthalate (PVAP) (Colorcon, West Point, Pa.); and Zein (alcohol-soluble protein extracted from corn gluten) (Freeman Industries, Tuckahoe, N.Y.). Agents for adjusting the pH that may be employed in a tablet include but are not limited to: physiological compatible acids or bases, acids such as citric acid, acetic acid, tartaric acid, bicarbonic acid, boric acid, phosphoric acids, tromethamine hydrochloric acid, and others. Bases that can be employed include: sodium acetate, sodium citrates, sodium phosphates, sodium carbonate, tromethamine base, and sodium borate.

Detergents which may be employed in the practice of the invention include the following (the concentration levels used preferably are from about 0.001 to about 5% by weight). Nonionic detergents that may be employed include: alkylglucoside, igepal (GAF), neodol (Shell), polytergent (Olin), sterox (Monsanto), emulphogene (GAF), triton (Rohm & Haas), dexoycholate (Sigma, St. Louis, Mo. 63178), brij (ICI Americas, Wilmington, Del. 19897), tween (ICI Americas), pluronics (BASF), tetronics (BASF), pluracols (BASF), plurfac (BASF), Tergitol (Union Carbide), Alfonic (Conoco), surfonic (Texaco), silwet (Union Carbide), cremophor (BASF), plantaren (Henkel). Anionic detergents that may be employed include, for example, carboxymethylcellulose (AKZO), alkyl sulfosuccinates (Sherex), alkylsulfates (Henkel), dimethicone copolyol sulfosuccinate (Mcintyre Group Ltd. Chicago, Ill. 60632), alkyl sarcosinates (W. R. Grace & Co. Lexington, Mass. 02173), Carbopols (B. F. Goodrich, Cleveland, Ohio 44141), Fatty acids alkali metal salts (Aldrich). Zwitterionic detergents which may be employed include products such as, CHAPS (Sigma, St. Louis, Mo. 63178), N-dodecyl-N,N-dimethyl-3-ammonio-1-propanesulfonate (Lauryl sulfobetaine) (Sigma, St. Louis, Mo. 63178), alkyl glycinates (Sherex, Dublin, Ohio 43017), alkyl betaine, alkyl amidopropyl betaine and alkyl hydroxy sultaine (Sherex, Dublin, Ohio 43017), Alkyl amphoproprionate (Sherex, and Miranol Chemical Company, Inc. South Brunswick, N.J. 08810).

Protease enzymes that may be employed in connection with the invention include: subtilisin, in a concentration of from about 0.0001% to about 5% in which the protease activity ranges from about 20 to about 100 casein units/mg. Use of this protease is discussed in U.S. Pat. No. 4,690,773 which is hereby incorporated by reference in its entirety.

Binders that can be utilized with the invention include gelatin, sucrose, polyvinyl pyrrolidone (PVP), hydroxymethylcellulose, dextrin, dextran, alkylcelluloses, carboxyalkylcelluloses, and hydroxypropylmethylcellulose (HPMC). The concentration of such binders, when used with the invention, prefereably is from about 1 to about 10% by weight.

Fillers that can be used in the invention include the following: lactose, sucrose, mannitol, dextrose, fructose, sorbitol, polyols, water soluble celluloses. The concentration of each may be from about 10 to about 70%.

Disintegrating agents may also be employed, and a person of skill in the art could employ these agents in concentrations of from about 0.01 to about 10%: Alginic acid, microcrystalline celluloses, effervescent system (sodium bicarbonate plus tartaric acid or citric acid), polyvinyl pyrrolidone (PVP), carboxymethylcellulose, and carboxyalkylcelluloses.

Other antiadherants, lubricants, and glidants that potentially can be employed in the invention include: Polyethylene glycol 6000, D-L-lucine, sodium lauryl sulfate, sodium benzoate, alkylsulfates. The concentration of such compounds may be from about 0.1 to about 5%.

Dyes are sometimes used in contact lens disinfecting/cleaning solutions, such as for decorating the tablet or as an indicator (i.e. reminder). Non-toxic FDA approved food dyes are preferred, such as FD&C Blue No. 2, FD&C Blue No. 1. The concentration of such dyes is usually no more than about 0.00001 to about 0.005%.

In general, when the invention is employed in the form of a powder it may contain from about 10% to about 80% by weight of the monoperoxyphthalate salt and from about 20% to about 90% of detergent. Inert fillers, effervescing agents, and other additives known in the art for use with such solutions may be included if desired, and would still be within the scope of the invention. Further, other lens cleaning ingredients may be employed, such as protease (substilisin A or B).

In one method of the invention, a dry component having the perphthalate species is combined with a wet component such as saline or deionized water. The resulting aqueous solution may be used to treat or disinfect a contact lens.

By "dry component" it is meant a powder, granular, or tablet form of a composition of monoperphthalic acid in the form of a salt or ester. The dry component may be hydrated to form the aqueous suspension of the invention.

The words "wet component" simply refer to an aqueous solution which may be mixed with a dry component to form a disinfecting composition capable of treating contact lenses.

Various forms of the perphthalic acid compounds may be used in the lens disinfecting/cleaning compositions of this invention, including but not limited to the following: magnesium monoperphthalate hexahydrate, magnesium monoperoxyphthalate hydrates, calcium monoperphthalate, sodium monoperphthalates, sodium monoperoxyphthalates, potassium monoperphthalates, potassium monoperoxyphthalates, magnesium perphthalates, calcium perphthalates, potassium perphthalates, sodium perphthalates, sodium potassium perphthalates, potassium hydrogen perphthalates, sodium hydrogen perphthalate, potassium acid perphthalates, perphthalic acid, monoperphthalic acid, magnesium perphthalate hexahydrates, perphthalate hydrates, 1,2 benzenedicarboperoxoic acid alkali metal salts, 1,2 benzenedicarboperoxoic acid dialkali metal salts, 2-carboxy benzenecarboperoxoic acid salts, 2-carboxy benzenemonocarboperoxoic acid alkaline earth metal salts, 2-carboxy benzenemonocarboperoxoic acid alkali metal salts, 2-carboxy benzenemonocarboperoxoic acid alkali metal hydrate salts, 2-carboxy benzenemonocarboperoxoic acid alkaline earth metal hydrate salts, 3-carboxy benzenemonocarboperoxoic acid alkali metal salts, 3-carboxy benzenemonocarboperoxoic acid alkali metal hydrate salts, 3-carboxy benzenemonocarboperoxoic acid alkaline metal hexahydrate salts, 3-carboxy benzenemonocarboperoxoic acid alkaline metal salts, 4-carboxy benzenemonocarboperoxoic acid alkali metal hexahydrate salts, 4-carboxy benzenemonocarboperoxoic acid alkali metal salts, 4-carboxy benzenemonocarboperoxoic acid alkaline metal hydrate salts, 4-carboxy benzenemonocarboperoxoic acid alkaline metal salts, 5-carboxy benzenemonocarboperoxoic acid alkali metal salts, 5-carboxy benzenemonocarboperoxoic acid alkali metal hydrate salts, 5-carboxy benzenemonocarboperoxoic acid alkaline metal salts, 5-carboxy benzenemonocarboperoxoic acid alkaline metal hydrate salts, 1,2-benzene dicarboperoxoic acid alkaline earth metal salts, 1,2-benzene dicarboperoxoic acid alkaline earth metal hydrate salts, 1,2-benzene dicarboperoxoic acid monoalkali metal salts, 1,2-benzene dicarboperoxoic acid dialkali metal salts, 1,2-benzene dicarboperoxoic acid, 1,3-benzene dicarboperoxoic acid alkaline earth metal salts, 1,3 benzene dicarboperoxoic acid, 1,3-benzene dicarboperoxoic acid monoalkali metal salts, 1,3-benzene dicarboperoxoic acid dialkali metal salts, 1,4-benzene dicarboperoxoic acid, 1,4-benzene dicarboperoxoic acid monoalkali metal salts, 1,4-benzene dicarboperoxoic acid dialkali metal salts, 1,4-benzene dicarboperoxoic acid alkeline earth metal salts, 1,5-benzene dicarboperoxoic acid, 1,5-benzene dicarboperoxoic acid monoaliali metal salts, 1,5-benzene dicarboperoxoic acid dialkali metal salts, and 1,5-benzene dicarboperoxoic acid alkaline earth metal salts.

The concentration of the perphthalate compound is less than 0.5% by weight, and concentrations of about 0.25%, 0.125, and 0.06% by weight have been found to be effective, yet substantially nontoxic to the eye.

In the practice of the invention, the lenses may be cleaned by soaking, spraying, or any other method which would apply the composition to the lens. After removal from the eye, the lens is soaked in a saline solution and one may add one magnesium perphthalate containing tablet for a time period between 10 minutes and 4 hours. Then, the lens is disinfected, and is ready to wear with or without rinsing with the same saline solution.

Monoperoxyphthalates also may be provided in the form of a salt, or as a pharmaceutically acceptable ester. The cation associated with the monoperoxyphthalate may be an alkali metal, an alkaline earth metal, a nontoxic heavy metal, trimethylammonium ortriethylammonium. In one aspect of the invention, an aqueous contact lens treating composition is provided that comprises less than about 0.5% by weight of a monoperphthalate compound having the general structure:

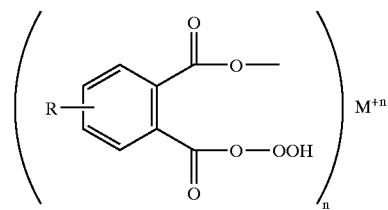

In connection with the above chemical structure, the R group is comprised of one or more substituents compatible with the peroxy acid functionality of the aromatic ring. By "substituents compatible with the peroxy acid functionality of the aromatic ring", as used herein, is meant substituents on the ring which do not react with peroxy acids thereby reducing the stability and effectiveness of the compounds to treat contact lenses. Nonlimiting examples of R groups include hydrogen, substituted and unsubstituted saturated alkyls having from 1 to about 20 carbon atoms (e.g., methyl, ethyl), substituted and unsubstituted aryl (e.g., phenyl, naphthyl), substituted and unsubstituted benzyl, chloro, bromo, iodo, fluoro, nitro, sulphonate, trifluoromethyl, trialkylammonium (e.g. trimethylammonium; triethylammonium), cyano, carboxy, carboxylate (e.g. $OCOCH_3$), percarboxylate (e.g. $CO_3H$), and alkoxy (e.g., methoxy, ethoxy). Preferred R groups are hydrogen, saturated alkyls having from 1 to about 20 carbon atoms, aryl, benzyl, chloro, fluoro, carboxy, and alkoxy. Particularly preferred for use in the above method for treating contact lenses is monoperphthalic acid (i.e., R=H), or its pharmaceutically acceptable salts or esters. R may also comprise an iodo, bromo, substituted or unsubstituted amino, or amido group, but such groups may be less desirable since they sometimes react with peroxy acid groups. Selection of substituents compatible with the peroxy acid functionality of the aromatic ring can easily be made by one skilled in the art.

Furthermore, a composition as provided above may be used with a chloride or other halide containing compound. In additional embodiments, the composition may be buffered to a pH of from about 4.0 to about 9, and desirably from about 6.0 to about 8.0. The composition may be provided in the form of a solid tablet which is soluble in aqueous solution, or alternatively may be provided in granular form as a powder or dry particulate.

Synthesis of substituted and unsubstituted monoperphthalic acid compounds may be achieved by those skilled in the art using methods disclosed in, for example, European Patent Application 27,693, published Apr. 29, 1981, filed by Interox Chemicals Limited; European Patent Application 66,992, to Interox Chemicals Limited; U.S. Pat. No. 3,075,921, to Brockelhurst et al.; "Organic Peroxides", Daniel Swern, Editor, published 1970 by John Wiley & Sons, Inc.; and in British Patent Specification 1,378,671; the disclosures of all of which are incorporated herein by reference. Synthesis of the magnesium salt of monoperphthalic acid is disclosed in the European Patent Application 27,693 published Apr. 29, 1981 (Interox Chemicals Limited). This compound is commercially available from Interox Chemicals Limited.

In general, magnesium perphthalate is not stable in aqueous solution. However, it is stable in solid form. Magnesium perphthalate is not compatible with chloride, and will react with chloride to form chlorine or chlorine derivatives, such as oxychloro compounds. Magnesium perphthalate in a chloride containing solution is not compatible with tinted lenses at high concentrations (>0.5%). In general, magnesium perphthalate in concentrations of about 0.25% and below are not toxic in a chloride or other halide-containing solution. Magnesium perphthalate may have significantly less anti-microbial activity if it is formulated in a solution not containing the chloride or other halide ion. However, magnesium perphthalate dissolved in a chloride or other halide-containing solution will represent a chlorine-or other halide-disinfecting system, and is effective at killing microbes. Further, the contact lenses used with this invention should be compatible with trace amounts of chlorine and oxychloro complexes or other halide and oxyhalocomplexes.

One possible lens disinfection system of this invention may include a tablet containing magnesium perphthalate or other perphthalate derivative with a solution containing chloride and/or other halide and buffer at approximately neutral pH, as previously described. EDTA (ethylenediaminotetraacetic acid) and Dequest 2060 are chelating agents which act to chelate metal ions such as iron, copper, magnesium, calcium and other metals, thereby reducing decomposition of hydrogen peroxide in solution. The metals are chelated in lens care solutions so they do not undesirably reduce hydrogen peroxide levels in the disinfecting solution. Dequest 2060 may be obtained from Monsanto Industrial Chemicals Co. located in St. Louis, Mo., or Solutia Inc., St. Louis, Mo.

Magnesium perphthalate in chloride-containing solutions is not generally compatible with tinted lenses at higher concentrations. Focus® brand royal blue lenses, for example, are generally more sensitive than Focus® aqua lenses. A Focus® royal blue lens is a Vifilcon[1]® lens material tinted by royal blue color reactive dye, and a Focus® aqua lens is that Vifilcon® lens material tinted by aqua color reactive dye. The lens material, Vifilcon® A, is a soft hydrophilic co-polymer of 2-hydroxyethyl methacrylate and povidone, USP. The chemical name is poly(2-hydroxethyl methacrylate-co-ethylene dimethacrylate co-methacrylic acid-g-povidone).

1 Vifilcon® is a registered trademark of CIBA Vision, Inc.

The "SoftWear® Saline" used in the Examples below is CIBA Vision SoftWear®[2] brand saline manufactured by CIBA Vision, Inc. of Duluth, Ga. The components of this saline include an antimicrobial buffer system (the A.B.S. system) which includes boric acid, sodium borate, sodium perborate (generating up to 0.006% hydrogen peroxide stabilized with phosponic acid). Essentially any commercially available lens saline could be used with the compositions of this invention, and this invention is not limited in its use or practice to the above-noted brand of saline solution.

2 "SOFTWEAR" is a registered trademark of CIBA Vision, Inc.

Saline solutions are indicated for use with soft (hydrophilic) contact lenses. Saline can be used as a rinsing solution following use of a daily or weekly cleaner or following disinfection, prior to lens insertion. Saline can also be used for storage after disinfection, or to dissolve enzyme tablets when sterile saline is required. Such saline solutions may also be used to dissolve tablets or powdered compositions of this invention.

In general, saline may be used to rinse lenses following cleaning, for rinsing following disinfection, or even as a lubricant prior to lens insertion. Saline may be used to dissolve enzyme tablets, or as a storage medium for soft lenses prior to disinfection, and for up to about 30 days following disinfection.

The compositions of this invention are effective in killing, and for a period of time preventing the re-growth, of aerobic and anaerobic bacteria. Thus, they are useful for treating or preventing topically-treatable aerobic and anaerobe infections, in humans or lower animals.

MEM Toxicity Testing Procedure

In testing the toxicity of compounds of the compositions disclosed in solution, an MEM test procedure is used. The MEM (Minimum Essential Medium) test procedure is employed to evaluate cytoxicity using standard USP (The United States Pharmacopeial Convention) elution assays. A description of the test procedure is provided herein.

The assay provides a means of evaluating extracts of polymeric materials under direct contact conditions. This method is appropriate for high-density materials and for dose-response evaluations.

All reagents should be tissue culture grade or equivalent and should be reconstituted in accordance with manufacturer's instructions using aseptic technique.

Media Preparation: 1× MEM media is prepared by mixing 100 mL Eagle's MEM (with Earl's Salts and Sodium Bicarbonate, without L-glutamine), with 10 mL serum, 1 mL-glutamine solution, and 0.5 mL antibiotic solution (L-glutamine and antibiotic solutions are purchased at correct concentrations and stored frozen at $-20°$ C.±2). Eagle's MEM is a sterile minimum essential medium and is available from Mediatech Celigro. Media may be stored up to 2 weeks at a temperature of $2°$ C.±2 after L-glutamine and antibiotics are added, or up to 1 month, if only serum is added.

Preparation of 0.25% Trypsin: 10× Trypsin is placed in sterile 50 ml centrifuge tubes in 4 ml aliquots and stored frozen at $-20°$ C.±2. Before use, a 4 ml aliquot of 10× trypsin is diluted 1:9 with 36 ml of Dulbecco's Phosphate Buffered Saline (PBS) to yield a 0.25% solution. Dulbecco's Saline is available from Mediatech Cellgro. Sterile 35 mm diameter petri dishes or 6 well tissue culture plates are used. Sterile serological pipets are employed in the procedure. Sterile absorbent material (e.g. Kay-Drys or similar material) is used. L929 mammalian fibroblasts (ATCC cell line CCL1, NCTC clone 929) are employed.

Overview of Method: Cell cultures are grown to a near confluent monolayer in 6 well plates (the wells are 35 mm). After the test, material is extracted under various conditions (i.e. extracting medium, time, temperature) so as to allow evaluation of extract toxicity in accordance with USP procedures. These procedures define methods to be used to extract materials for in vivo or in vitro toxicity evaluations in accordance with United States Pharmacopoeia (USP), and are hereby incorporated by reference. The Sodium Chloride Injection extract is diluted with serum-supplemented cell culture medium at 25% extract concentration. Each culture is examined microscopically after 48 hours using trypan blue for the presence of morphological changes, reduction in cell density or cell lysis induced by the test material.

Cell Layer Preparation: The next step is to tryptanize cells. Next, one determines cell density using standard methods to define standard cell biology methods to be used to determine and adjust the concentration of a cell suspension, i.e. cell density.

Then, an adjustment is made to yield a standard cell suspension with a density of 250,000 to 350,000 cell/mL in serum supplemented MEM for L929 cells. Seed cells are placed into 6 well plates by pipetting 2 ml of the standard cell suspension into each well. Next, one rotates in two directions to ensure even distribution of cells throughout the entire surface of the well.

The plates are incubated at $37°$ C.±2 in a humidified incubator with an atmosphere of 5% $CO_2$±1 in air until the cell monolayer is near-confluent by microscopic examination (approximately 48 hours).

Exposure to Test Extracts: Exposure to test extracts is determined examining a representative prepared cell culture plate using the microscope to observe the cell monolayer for correct confluency. Each experiment includes positive and negative control samples in order to ensure normal biological responses for the cell cultures. While any sample which produces reproducible cytotoxic responses may be employed as judged appropriate, typical controls are as follows:

Positive Control: Cell cultures exposed for 48 hours to 5 ppm and 50 ppm BAK in serum-supplemented MEM at $37°$ C.±2 in a humidified atmosphere of 5%±1 $CO_2$ in air.

Negative Control: USP Negative BioReaction RS in serum-supplemented MEM.

Evaluation of Cytotoxic Response/Vital Staining Methods: Evaluation begins by removing cultures from the incubator following the test period. Next, aspirate off the medium and apply the vital stain by pipetting 0.8 mL of 0.1% trypan blue in PBS to each culture.

After approximately 1 minute exposure to the trypan blue solution, remove excess dye and gently rinse monolayer with 1 ml PBS. Remove PBS and evaluate each culture microscopically for evidence of cytotoxicity as indicated by trypan blue staining, morphological changes, and/or decrease in cell density.

Results: USP Standard Elution Toxicity

Results are reported based on Reactivity Grades, as set forth below.

TABLE 1

| Grade | Reactivity | Condition of all Cultures |
| --- | --- | --- |
| 0 | None | No cell lysis—Discrete intracytoplasmic granules |
| 1 | Slight | Not more than 20% of cells round and loosely attached—occasional lysed cells present |
| 2 | Mild | Not more than 50% of cells round—extensive cell lysis and empty areas between cells |
| 3 | Moderate | Not more than 70% of the cell layers contain rounded cells and/or lysed |
| 4 | Severe | Nearly complete destruction of the cell layer |

The present invention may be better understood by referring to the examples set forth below.

EXAMPLE 1

A solution of 0.5% boric acid, 0.61% sodium chloride, 120 ppm dequest 2060, and 0.25% magnesium monoperphthalate hexahydrate (Aldrich, tech. 80%) was pH adjusted to 6.877 by either diluted sodium hydroxide solution or diluted hydrochloric acid solution. The solution was made sterile by microfiltration. Antimicrobial tests were conducted as soon as received, and produced results seen on Table 2. In-vitro toxicity tests using the MEM procedure outlined above are shown in Table 3.

EXAMPLE 2

A solution without magnesium perphthalate to be used as a control was prepared. A solution of 0.5% boric acid, 0.61% sodium chloride, 120 ppm dequest 2060, 0.1% sodium perborate (equivalent to 219 ppm hydrogen peroxide), with the pH was adjusted to 6.878 by either diluted sodium hydroxide solution or diluted hydrochloric acid solution. The solution was made sterile by microfiltration. Antimicrobial tests were conducted as soon as received, and produced results seen on Table 2. In-vitro toxicity tests using the MEM procedure outlined above are shown in Table 3.

EXAMPLE 3

A solution was prepared as in Example 1, except that the concentration of magnesium perphthalate was only one-half as much (0.125%). Antimicrobial tests were conducted as soon as received, and produced results seen on Table 2. "SA" refers to Staphylococcus aureus and "CA" refers to Candida albicans. Times shown are elapsed time. In-vitro toxicity tests using the MEM procedure outlined above are shown in Table 3.

EXAMPLE 4

A solution was prepared as in Example 1, except that the concentration of magnesium perphthalate was only one-fourth as much as in Example 1 (0.063%). Antimicrobial tests were conducted as soon as received, and produced results seen on Table 2. In-vitro toxicity tests using the MEM procedure outlined above are shown in Table 3.

TABLE 2

Antimicrobial Results

| Example | SA (0 hr) | SA (10 min) | (1 hr.) | (4 hr.) | CA (0 hr) | CA (10 min) | (1 hr.) | (4 hr.) |
|---|---|---|---|---|---|---|---|---|
| 1 | 2.4E5 | | <10 | <10 | 7.3E5 | | <10 | <10 |
| 2 (control) | 2.4E5 | | 2.5E5 | 2.2E5 | 7.3E5 | | 7.0E5 | 3.5E5 |
| 2 (control) | 3.3E5 | 3.2E5 | | 3.6E5 | 8.0E5 | 7.7E5 | | 7.8E5 |
| 3 | 3.3E5 | <10 | | <10 | 8.0E5 | <10 | | <10 |
| 4 | 3.3E5 | <10 | | <10 | 8.0E5 | <10 | | <10 |

In-vitro toxicity results are listed in Table 3 below:

TABLE 3

| Example | MEM Result |
|---|---|
| 1 | 1-1-1 |
| 2 | 4-4-4 |
| 3 | 1-1-1 |
| 4 | 0-0-0 |
| Softwear saline | 1-1-1 |

Note regarding MEM Testing Results:
0: 0% cell turns blue,
1: 1% to 20% cells turn blue,
2: 21% to 50% cells turn blue,
3: 51% to 70% cells turn blue,
4: 71% to 100% cells turn blue.

EXAMPLE 5

Magnesium Perphthalate Testing

In-vitro toxicity tests of various concentrations of magnesium perphthalate with saline solution and without saline solution by MEM test procedures were conducted.

The "SoftWear® Saline" used was the CIBAVision brand saline manufactured by CIBA Vision of Duluth, Ga. The components of this saline solution include an antimicrobial buffer system (the A.B.S. system) which includes boric acid, sodium borate, sodium perborate (generating up to 0.006% hydrogen peroxide-stabilized with phosponic acid).

The results of Example 5 are shown in Table 4 below.

TABLE 4

Magnesium Perphthalate Testing

| Formulation number | Formulation | MEM result | With or without saline |
|---|---|---|---|
| 0990303-1 | softwear saline | 1, 1, 1<br>1, 1, 1 | With |
| 0990303-2 | 0.056% Sodium perborate, 0.12% MgCl2 in Softwear saline buffer with 120 ppm dequest 2060, pH adjusted to 6.938. | 4, 4, 4<br>4, 4, 4 | With |
| 0990303-3 | 0.25% Magnesium perphthalate in Softwear saline buffer (without sodium perborate) with 120 ppm dequest 2060, pH adjusted to 6.865 | 1, 1, 1<br>1, 1, 1 | With |
| 0990303-4 | The same as above, 0990303-3, except 100 ppm H2O2 withoutMagnesium perphthalate, pH adjusted to 6.978 | 1, 1, 1<br>1, 1, 1 | With |
| 0990303-5 | The same as above 0990303-3, except 0.06% Magnesium perphthalate, pH adjusted to 6.958 | 0, 0, 0,<br>0, 0, 0 | With |
| 0990317-11 | 0.25% Magnesium perphthalate in Softwear saline buffer with 120 ppm dequest 2060, pH adjusted to 6.944. | 0, 0, 0<br>0, 0, 0 | With |
| 0990317-12 | The same as above, 0990317-11, except 0.12% Magnesium perphthalate, pH adjusted to 6.974 | 0, 0, 0<br>0, 0, 0 | with |
| 0990317-13 | The same as above, except 0.06% Magnesium perphthalate, pH adjusted to 6.965 | 0, 0, 0<br>0, 0, 0 | with |
| 0990317-14 | The same as 0990317-11, except heated at 100 C. for 24 hrs. | 0, 0, 1<br>1, 0, 0 | with |
| 0990317-15 | The same as 0990317-11, except 137 ppm H2O2, pH adjusted to 6.848 | 4, 4, 4<br>4, 4, 4<br>(all cells dead) | with |
| 0990526-1 | 0.5% Magnesium perphthalate in 3.5% sorbitol, 0.0622% sodium phosphate dibasic anhy., pH adjusted to 6.818 | 4, 4, 4<br>4, 4, 4<br>(all cells dead) | without |
| 0990526-2 | The same as above, 0990526-1, except 0.25% Magnesium perphthalate, pH adjusted to 6.819 | 1, 1, 1<br>1, 1, 1<br>(2% cells dead) | without |
| 0990526-3 | The same as above. 0990526-1, except 0.06% Magnesium perphthalate, pH adjusted to 6.842 | 1, 1, 1<br>1, 1, 1<br>(2–3% cells dead) | without |
| 0990526-4 | The same as above, 0990526-1, except 100 ppm H2O2, pH adjusted to 6.949 | 2, 2, 2<br>2, 2, 2<br>(cells removed + cell growth inhibition, 40% cells dead) | without |

EXAMPLE 6

Magnesium Perphthalate Tested at Various Concentration Levels

Additional data was obtained to determine the effect of magnesium perphthalate when used as a lens disinfecting and cleaning agent with and without saline. At concentrations of 0.5% and above, toxicity was determined to be at a level "4" MEM (all cells dead). However, at concentrations below 0.5%, the toxicity was found to be generally at about a MEM Test Result level 1 (2–3% or less cells dead). Some test results at below 0.5%. magnesium perphthalate showed an MEM Result of "0" (no cell lysis at all), as shown below in Table 5.

TABLE 5

Magnesium Perphthalate Toxicity Testing

| Formulation number | Formulation | % of magnesium perphthalate | With without saline | MEM result |
|---|---|---|---|---|
| 0990303-3 | 0.25% Magnesium perphthalate in softwear saline buffer (without sodium perborate) pH = 6.865 | 0.25 | with | 1, 1, 1 1, 1, 1 |
| 0990303-4 | The same as 0990303-3, except 0.125% Magnesium perphthalate, pH = 6.978 | 0.125 | with | 1, 1, 1 1, 1, 1 |
| 0990303-5 | The same as 0990303-3, except 0.06% Magnesium perphthalate, pH = 6.958 | 0.06 | with | 0, 0, 0 0, 0, 0 |
| 0990317-11 | The same as 0990303-3, repeat | 0.25 | with | 0, 0, 0 0, 0, 0 |
| 0990317-12 | The same as 0990303-4, repeat | 0.125 | with | 0, 0, 0 0, 0, 0 |
| 0990317-13 | The same as 0990303-5, repeat | 0.06 | with | 0, 0, 0 0, 0, 0 |
| 0990317-14 | The same as 0990317-11, except heated at 100° C. for 24 hrs. | 0.25 | with | 0, 0, 1 1, 0, 0 |
| 0990526-1 | 0.5% Magnesium perphthalate in 3.5% sorbitol, 0.0622% sodium phosphate dibasic anhy., pH = 6.818 | 0.5 | without | 4, 4, 4 4, 4, 4 |
| 0990526-2 | The same as 0990526-1, except 0.25% Magnesium perphthalate, pH = 6.819 | 0.25 | without | 1, 1, 1 1, 1, 1 |
| 0990526-3 | The same as 0990526-1, except 0.06% Magnesium perphthalate, pH = 6.842 | 0.06 | without | 1, 1, 1 1, 1, 1 |
| 0990922-1 | 1.0% Magnesium perphthalate in 0.9% sodium bicarbonate, 1.2% sodium sulfate anhy., 0.5% boric acid, and 0.0229% sodium perborate, pH = 7.090 | 1.0 | without | 4, 4, 4 4, 4, 4 |
| 0990922-2 | The same as 0990922-1, except 0.5% Magnesium perphthalate and 0.45% sodium bicarbonate | 0.5 | without | 4, 4, 4 4, 4, 4 |
| 0990922-3 | The same as 0990922-1, except 0.25% Magnesium perphthalate and 0.225% sodium bicarbonate | 0.25 | without | 2, 2, 2 2, 2, 2 |
| 0990922-4 | The same as 0990922-1, except 0.125% Magnesium perphthalate and 0.1125% sodium bicarbonate | 0.125 | without | 1, 1, 1 1, 1, 1 |
| 0990922-5 | 1.0% Magnesium perphthalate in 0.9% sodium bicarbonate, 0.61% sodium chloride, 0.5% boric acid and 0.0229% sodium perborate, pH = 7.133 | 1.0 | with | 4, 4, 4 4, 4, 4 |
| 0990922-6 | The same as 0990922-5, except 0.5% Magnesium perphthalate and 0.45% sodium bicarbonate | 0.5 | with | 4, 4, 4 4, 4, 4 |
| 0990922-7 | The same as 0990922-5, except 0.25% Magnesium perphthalate and 0.225% sodium bicarbonate | 0.25 | with | 1, 1, 1 1, 1, 1 |
| 0990922-8 | The same as 0990922-5, except 0.125% Magnesium perphthalate and 0.1125% sodium bicarbonate | 0.125 | with | 1, 1, 1 1, 1, 1 |

EXAMPLE 7

An aqueous contact lens disinfecting and cleaning solution of 0.012 g of magnesium monoperphthalate hexahydrate and 0.012 g of sodium bicarbonate in 20 ml of Softwear® saline with one tablet of Unizyme® was prepared. "Unizyme" is an enzymatic cleaner (tablet) formulated to remove protein deposits from soft (hydrophilic) contact lenses. It contains subtilisin A, potassium carbonate, citric acid, polyethylene glycol, and sodium benzoate. Next, the lens was soaked in 2 ml of this solution for at least for 4 hours.

EXAMPLE 8

An aqueous contact lens disinfecting and cleaning solution of 0.012 g of magnesium monoperphthalate hexahydrate in 20 ml of Softwear® saline with one tablet of Unizyme® was prepared. Next, the protein treated Vilfilcon® contact lens was soaked in 2 ml of this solution for at least for 4 hours. In the case of a protein treated lens, the following was performed: the clean or new Vilficon® lens was soaked in a solution containing 0.12% lysozyme and 0.388% albumin in Softwear® Saline for at least about 4 hours.

EXAMPLE 9

An aqueous contact lens disinfecting and cleaning solution of 0.012 g of magnesium monoperphthalate hexahydrate and 0.012 g sodium bicarbonate in 20 ml of Softwear® saline was prepared. Next, the protein treated Vilfilcon® lens was soaked in 2 ml of this solution for at least for 4 hours.

EXAMPLE 10

An aqueous contact lens disinfecting and cleaning solution of 0.25% magnesium monoperphthalate hexahydrate, 0.25% sodium bicarbonate, and 0.01% sodium octanoate in Softwear® saline was prepared. Next, the protein treated Vilfilcon® lens was soaked in 2 ml of this solution for at least for about 4 hours. The cleaning efficacy results of the vilfilcon lens in Examples 7 to 10 are shown in the Table 6 below. The equation to calculate lens cleanness is based on a % transmittance of 400 nm. The equation is expressed as:

$$\% \text{ cleanness} = \frac{\left[\left(\frac{\% \text{ transmittance treated lens} - }{\% \text{ transmittance new lens}}\right)\right]}{33.84} + 1 \times 100\%$$

TABLE 6

Cleaning Efficacy in Different Formulations

| Example | Number of Cycles | The lens cleanness* (%), |
|---------|------------------|--------------------------|
| 7 | 28 | 76.1 |
| 9 | 28 | 0 |
| 9 | 4 | 34.7 |
| 10 | From 5 to 6 | 32.5 to 46.9 |

These and other modifications and variations to the present invention may be practiced by those of ordinary skill in the art without departing from the spirit and scope of the invention. The invention is particularly set forth in the appended claims. Further, it should be understood that aspects of the various embodiments disclosed in this specification may be interchanged both in whole or in part, without departing from the invention. Furthermore, those of ordinary skill in the art will appreciate that this description is by way of examples only, and is not intended to limit the invention as described in the claims.

What is claimed is:

1. A low toxicity compound for treating contact tenses in aqueous solution, comprising a compound that is effective at an aqueous concentration of no more than about 0.5% by weight of said solution, said compound being selected from the group of compounds consisting of: magnesium monoperphthalate hexahydrate, magnesium monoperoxyphthalate hydrates, calcium monoperphthalate, sodium monoperphthalates, sodium monoperoxyphthalates, potassium monoperphthalates, potassium monoperoxyphthalates, magnesium perphthalates, calcium perphthalates, potassium perphthalates, sodium perphthalates, sodium potassium perphthalates, potassium hydrogen perphthalates, sodium hydrogen perphthalate, potassium acid perphthalates, perphthalic acid, monoperphthalic acid, magnesium perphthalate hexahydrates, perphthalate hydrates, 1,2 benzenedicarboperoxoic acid alkali metal salts, 1,2 benzenedicarboperoxoic acid dialkali metal salts, 2-carboxy benzenecarboperoxoic acid salts, 2-carboxy benzenemonocarboperoxoic acid alkaline earth metal salts, 2-carboxy benzenemonocarboperoxoic acid alkali metal salts, 2-carboxy benzenemonocarboperoxoic acid alkali metal hydrate salts, 2-carboxy benzenemonocarboperoxoic acid alkaline earth metal hydrate salts, 3-carboxy benzenemonocarboperoxoic acid alkali metal salts, 3-carboxy benzenemonocarboperoxoic acid alkali metal hydrate salts, 3-carboxy benzenemonocarboperoxoic acid alkaline metal hexahydrate salts, 3-carboxy benzenemonocarboperoxoic acid alkaline metal salts, 4-carboxy benzenemonocarboperoxoic acid alkali metal hexahydrate salts, 4-carboxy benzenemonocarboperoxoic acid alkali metal salts, 4-carboxy benzenemonocarboperoxoic acid alkaline metal hydrate salts, 4-carboxy benzenemonocarboperoxoic acid alkaline metal salts, 5-carboxy benzenemonocarboperoxoic acid alkali metal salts, 5-carboxy benzenemonocarboperoxoic acid alkali metal hydrate salts, 5-carboxy benzenemonocarboperoxoic acid alkaline metal salts, 5-carboxy benzenemonocarboperoxoic acid alkaline metal hydrate salts, 1,2-benzene dicarboperoxoic acid alkaline earth metal salts, 1,2-benzene dicarboperoxoic acid alkaline earth metal hydrate salts, 1,2-benzene dicarboperoxoic acid monoalkali metal salts, 1,2-benzene dicarboperoxoic acid dialkali metal salts, 1,2-benzene dicarboperoxoic acid, 1,3-benzene dicarboperoxoic acid alkaline earth metal salts, 1,3 benzene dicarboperoxoic acid, 1,3-benzene dicarboperoxoic acid monoalkali metal salts, 1,3-benzene dicarboperoxoic acid dialkali metal salts, 1,4-benzene dicarboperoxoic acid, 1,4-benzene dicarboperoxoic acid monoalkali metal salts, 1,4-benzene dicarboperoxoic acid dialkali metal salts, 1,4-benzene dicarboperoxoic acid alkeline earth metal salts, 1,5-benzene dicarboperoxoic acid, 1,5-benzene dicarboperoxoic acid monoaliali metal salts, 1,5-benzene dicarboperoxoic acid dialkali metal salts, and 1,5-benzene dicarboperoxoic acid alkaline earth metal salts.

2. An aqueous contact lens treating composition comprising: less than about 0.5% by weight of a monoperphthalate compound having the general structure:

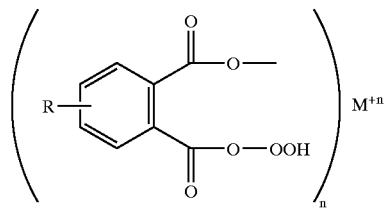

or its pharmaceutically acceptable salts or esters, wherein $M^{+n}$ is a cation selected from the group consisting of an alkali metal, an alkaline earth metal, a nontoxic heavy metal, trimethyl ammonium and triethylammonium, and R is 1 or more substituents compatible with the peroxy acid functionality of the aromatic ring.

3. The composition of claim 2 further comprising a chloride-containing compound.

4. The composition of claim 2 wherein the composition is buffered such that during treating of the contact lens the composition has a pH of from about 6 to about 7.

5. A composition as in claim 2 in which the monoperphthalate compound is magnesium monoperphthalate.

6. The composition of claim 2 in which the composition comprises about 0.25% by weight of the monoperphthalate compound.

7. The composition of claim 2 in which the $M^{+n}$ cation is selected from the group consisting of: sodium, magnesium, and potassium.

8. A tablet for treating a contact lens, comprising:
a first compound having relatively low biological toxicity in aqueous solution, wherein the first compound is effective at an aqueous concentration of no more than about 0.5% by weight of said compound in aqueous solution, said first compound being selected from the group consisting of:
magnesium monoperphthalate hexahydrate, magnesium monoperoxyphthalate hydrates, calcium monoperphthalate, sodium monoperphthalates, sodium monoperoxyphthalates, potassium monoperphthalates, potassium monoperoxyphthalates, magnesium perphthalates, calcium perphthalates, potassium perphthalates, sodium perphthalates, sodium potassium perphthalates, potassium hydrogen perphthalates, sodium hydrogen perphthalate, potassium acid perphthalates, perphthalic acid, monoperphthalic acid, magnesium perphthalate hexahydrates, perphthalate hydrates, 1,2 benzenedicarboperoxoic acid alkali metal salts, 1,2 benzenedicarboperoxoic acid dialkali metal salts, 2-carboxy benzenecarboperoxoic acid salts, 2-carboxy benzenemonocarboperoxoic acid alkaline earth metal salts, 2-carboxy benzenemonocarboperoxoic acid alkali metal salts, 2-carboxy benzenemonocarboperoxoic acid alkali metal hydrate salts, 2-carboxy benzenemonocarboperoxoic acid alkaline earth metal hydrate salts, 3-carboxy benzenemonocarboperoxoic acid alkali metal salts, 3-carboxy benzenemonocarboperoxoic acid alkali metal hydrate salts, 3-carboxy benzenemonocarboperoxoic acid alkaline metal hexahydrate salts, 3-carboxy benzenemonocarboperoxoic acid alkaline metal salts, 4-carboxy benzenemonocarboperoxoic acid alkali metal hexahydrate salts, 4-carboxy benzenemonocarboperoxoic acid alkali metal salts, 4-carboxy benzenemonocarboperoxoic acid alkaline metal hydrate salts, 4-carboxy benzenemonocarboperoxoic acid alkaline metal salts, 5-carboxy benzenemonocarboperoxoic acid alkali metal salts, 5-carboxy benzenemonocarboperoxoic acid alkali metal hydrate salts, 5-carboxy benzenemonocarboperoxoic acid alkaline metal salts, 5-carboxy benzenemonocarboperoxoic acid alkaline metal hydrate salts, 1,2-benzene dicarboperoxoic acid alkaline earth metal salts, 1,2-benzene dicarboperoxoic acid alkaline earth metal hydrate salts, 1,2-benzene dicarboperoxoic acid monoalkali metal salts, 1,2-benzene dicarboperoxoic acid dialkali metal salts, 1,2-benzene dicarboperoxoic acid, 1,3-benzene dicarboperoxoic acid alkaline earth metal salts, 1,3 benzene dicarboperoxoic acid, 1,3-benzene dicarboperoxoic acid monoalkali metal salts, 1,3-benzene dicarboperoxoic acid dialkali metal salts, 1,4-benzene dicarboperoxoic acid, 1,4-benzene dicarboperoxoic acid monoalkali metal salts, 1,4-benzene dicarboperoxoic acid dialkali metal salts, 1,4-benzene dicarboperoxoic acid alkeline earth metal salts, 1,5-benzene dicarboperoxoic acid, 1,5-benzene dicarboperoxoic acid monoaliali metal salts, 1,5-benzene dicarboperoxoic acid dialkali metal salts, and 1,5-benzene dicarboperoxoic acid alkaline earth metal salts.

9. A tablet for treating a contact lens, the tablet adapted for dissolving in aqueous solution to provide a substantially nontoxic lens disinfecting solution, the tablet comprising:

a monoperphthalate compound having the general structure:

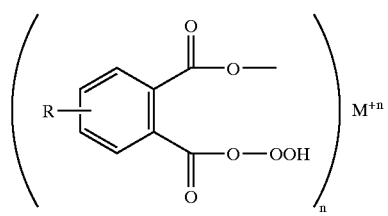

or its pharmaceuticaily acceptable salts or esters, wherein $M^{+n}$ is a cation selected from the group consisting of an alkali metal, an alkaline earth metal, a nontoxic heavy metal, trimethyl ammonium and triethylammonium, and R is 1 or more substituents compatible with the peroxy acid functionality of the aromatic ring.

\* \* \* \* \*